US008686183B2

(12) United States Patent
Clarke et al.

(10) Patent No.: US 8,686,183 B2
(45) Date of Patent: Apr. 1, 2014

(54) METAL-CATALYSED CARBONYLATION OF UNSATURATED COMPOUNDS

(75) Inventors: Matthew Lee Clarke, Fife (GB); Tina Marie Konrad, Fife (GB)

(73) Assignee: University Court Of The University of St Andrews (GB)

( * ) Notice: Subject to any disclaimer, the term of this patent is extended or adjusted under 35 U.S.C. 154(b) by 111 days.

(21) Appl. No.: 13/394,946

(22) PCT Filed: Sep. 10, 2010

(86) PCT No.: PCT/GB2010/001715
§ 371 (c)(1),
(2), (4) Date: Mar. 30, 2012

(87) PCT Pub. No.: WO2011/030110
PCT Pub. Date: Mar. 17, 2011

(65) Prior Publication Data
US 2012/0178963 A1 Jul. 12, 2012

(30) Foreign Application Priority Data

Sep. 11, 2009 (GB) .................................. 0915946.8

(51) Int. Cl.
| C07C 51/14 | (2006.01) |
| C07C 67/38 | (2006.01) |
| B01J 31/12 | (2006.01) |
| B01J 27/185 | (2006.01) |

(52) U.S. Cl.
USPC ........... 562/406; 562/502; 560/103; 560/106; 560/109; 560/233; 502/162; 502/213

(58) Field of Classification Search
None
See application file for complete search history.

(56) References Cited

U.S. PATENT DOCUMENTS

| 2003/0055253 A1 | 3/2003 | Ahlers et al. |
| 2004/0236134 A1 | 11/2004 | Schmutzler et al. |

FOREIGN PATENT DOCUMENTS

| WO | WO 97/47632 A1 | 12/1997 |
| WO | WO 02/057278 A1 | 7/2002 |
| WO | WO 2004/111065 A1 | 12/2004 |
| WO | WO 2008/124468 A1 | 10/2008 |
| WO | WO 2009/055912 A1 | 5/2009 |

OTHER PUBLICATIONS

Search Report corresponding to Application No. GB0915946.8 dated Jan. 11, 2010.
Csók et al. "Carbonylation (hydroformylation and hydrocarbalkoxylation) reactions in the presence of transition metal: p-tert-butyl-calix[4]arene-based phosphine and phosphinite systems", J. Organometallic Chem. 570"23-29 (1998).
Notification of Transmittal of the International Search Report and the Written Opinion of the International Searching Authority, or the Declaration corresponding to PCT/GB2010/001715 mailed Jul. 4, 2011.
Brennführer et al. "Palladium-Catalyzed Carbonylation Reactions of Aryl Halides and Related Compounds", Angew. Chem. Int. Ed. 48(23):4114-4133 (2009).
Brennführer "Palladium/di-1-adamantyl-$n$-butylphosphine-catalyzed Carbonylation Reactions", Leibniz-Institut für Katalyze e.V. an der Universität Rostock 119 pages (2008).
Frew et al. "Palladium(II) Complexes of New Bulky Bidentate Phosphanes: Active and Highly Regioselective Catalysts for the Hydroxycarbonylation of Styrene", Chem. Eur. J. 15(40):10504-10513 (2009).
Written Opinion of the International Preliminary Examining Authority corresponding to PCT/GB2010/001715 mailed Nov. 2, 2011.
Dyer et al. "The First Structural Characterization of a [2.2]PHANEPHOS-Transition-Metal Complex: Structure of rac-[Pd(4,12-bis(diphenylphosphino)[2.2]paracyclophane)CL$_2$l]", Organometallics 17:4344-4346 (1998).
Dekker et al. "Influence of ligands and anions on the insertion of alkenes into palladium-acyl and palladium-carbomethoxy bonds in the neutral complex (dppp)Pd(C(O)CH$_3$)Cl and the ionic complexes [(P-P)PdR(L)]$^+$SO$_3$CF$^-_3$ (P-P = dppe, dppp, dppb; R = C(O)CH$_3$, L = CH$_3$CN, PPH$_3$; R = C(O)OCH$_3$, L = PPH$_3$)", J. Organometallic Chem. 430:357-372 (1992).
Dominguez et al. "Electrophilic Substitution of Dibromoparacyclophane: A Route to Novel Paracyclophane Phosphine Ligands", Organic Letters 6(12):1927-1930 (2004).
Fanjul et al. "Palladium Complexes of the Heterodiphosphine $o$-C$_6$H$_4$(CH$_2$P$^t$Bu$_2$)(CH$_2$PPh$_2$) Are Highly Selective and Robust Catalysts for the Hydromethoxycarbonylation of Ethene", Organometallics 29:2292-2305 (2010).
Sherrill et al. "Rhodium-Catalyzed Hydroformylation of Cyclopropenes", J. Am. Chem. Soc. 130:13804-13809 (2008)
Liu et al. "The Mechanism of the Hydroalkoxycarbonylation of Ethene and Alkene—CO Copolymerization Catalyzed by Pd$^{11}$-Diphosphine Cations", Chem. Eur. J. 12:4417-4430 (2006).
Eastham et al. "Deuterium labeling evidence for a hybride mechanism in the formation of methyl propanoate from carbon monoxide, ethane and methanol catalyzed by a palladium complex", J. Chem. Soc., Dalton Trans. 1613-1617 (2002).
Clegg et al. "Highly active and selective catalysts for the production of methyl propanoate via the methoxycarbonylation of ethane", Chem. Commun. 1877-1878 (1999).
Rio et al. "Hydroxycarbonylation of styrene with palladium catalysts the influence of the mono- and bidentate phosphorus ligand", J. Molecular Catalysis A: Chemical 161:39-48 (2000).

(Continued)

Primary Examiner — Brian J Davis
(74) Attorney, Agent, or Firm — Myers Bigel Sibley & Sajovec, P.A.

(57) ABSTRACT

The invention provides a method for the hydroxycarbonylation, alkoxycarbonylation, aryloxycarbonylation or thiocarbonylation of an unsaturated molecule. The method includes a hydroxycarbonylation, alkoxycarbonylation, aryloxycarbonylationor thiocarbonylation reaction on the unsaturated molecule in which a complex including a ligand comprising a [n,n'] cyclophane comprising two non-fused monocyclic aromatic rings bridged by two linear and aliphatic linkages, in which each of the non-fused monocyclic aromatic rings is substituted with a phosphorus atom-containing substituent, is used to catalyse the reaction.

21 Claims, 1 Drawing Sheet

(56) References Cited

OTHER PUBLICATIONS

West et al. "Synthesis, Molecular Structure, and Properties of *in*-Phosphaphanes with Substituted Basal Aromatic Rings", *J. Org. Chem.* 58:3502-3506 (1993).

Hart et al. "2'-Substituted Meta-terphenyls as Building Blocks for Cyclophanes with Intra-Annular Functionality", *Tetrahedron* 51(5):1313-1336 (1995).

Azerraf et al. "Roof-Shaped Halide-Bridged Bimetallic Complexes via Ring Expansion Reaction", *Inorganic Chem.* 45:7010-7017 (2006).

Grossman et al. "Palladium Complexes Bearing Novel Strongly Bent Trans-Spanning Diphosphine Ligands: Synthesis, Characterization, and Catalytic Activity", *Organometallics* 25:375-381 (2006).

El-Qisairi et al. "Oxidation of olefins by palladium(II) Part 17. An asymmetric chlorohydrins synthesis catalyzed by a bimetallic palladium(II) complex", *J. Organometallic Chem*, 603:50-60 (2000).

El-Qisairi et al. "Oxidation of olefins by palladium(II). 18. Effect of reaction conditions, substrate structure and chiral ligand on the bimetallic palladium(II) catalyzed asymmetric chlorohydrins synthesis", *J. Organometallic Chem.* 656:168-176 (2002).

Invitation to Pay Additional Fees and, Where Applicable, Protest Fee corresponding to PCT/GB2010/001715 mailed Mar. 2, 2011.

Chapter II Demand corresponding to PCT/GB2010/001715 dated Sep. 22, 2011.

Response to Written Opinion corresponding to PCT/GB2010/001715 mailed Nov. 29, 2011.

Notification of the International Preliminary Report on Patentability corresponding to PCT/GB2010/001715 mailed Jan. 24, 2012.

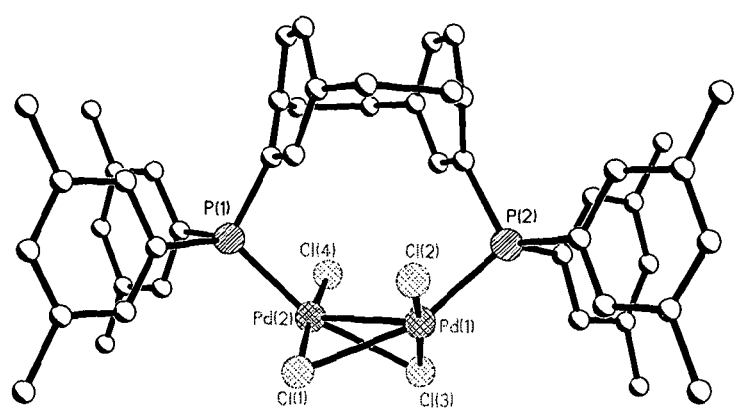

METAL-CATALYSED CARBONYLATION OF UNSATURATED COMPOUNDS

RELATED APPLICATIONS

This application is a 35 U.S.C. §371 national stage application of PCT Application No. PCT/GB2010/001715, filed on Sep. 10, 2010, which claims priority from British Application No. 0915946.8 filed on Sep. 11, 2009, the contents of which are incorporated herein by reference in their entireties. The above-referenced PCT International Application was published as International Publication No. WO 2011/030110 A2 on Mar. 17, 2011.

FIELD OF THE INVENTION

The invention relates to processes in which unsaturated compounds are reacted with carbon monoxide and water, an alcohol, e.g. a phenol or a thiol, for example water or an alcohol, to generate carboxylic acid derivatives, and to complexes for use in such processes.

BACKGROUND TO THE INVENTION

Hydroxy- and alkoxycarbonylation of unsaturated compounds such as alkenes and alkynes (also referred to in the art as hydrocarbonylation and hydroesterification respectively) are very useful reactions in synthetic chemistry. They can deliver carboxylic acid derivatives (acids, esters) in one step with essentially no waste products. Consequentially these reactions are often used in the production of bulk chemicals and fine chemicals, and potentially useful in the synthesis of pharmaceutically active compounds.

I del Rio et al. (*J. Mol. Catal. A-Chem.*, 2000, 161, 39-48), in a report into the palladium-catalysed hydroxycarbonylation of styrene, compared the effect of monodentate phosphine and bidentate diphosphine ligands. Whilst bidentate diphosphine ligands are reported as having certain advantages, this publication also describes how hydroxycarbonylations require significantly more forcing conditions when diphosphines are used as ligands, with typical temperatures of around 150° C. J J R Frew et al. (*Dalton Trans.*, 2008, 1976) also describe examples of hydroxycarbonylation reactions in which certain diphosphines allow good yields at lower temperatures (ca. 100° C.) to be achieved. In these reports, monomeric palladium catalysts are described—in which a single palladium centre is chelated by the phosphorus atoms in the diphosphine—or catalysts formed in situ from an excess of diphosphine ligand relative to palladium under conditions in which the stoichiometry of reactants means that the formation of monomeric palladium catalysts may be expected.

The use of dimeric catalysts in methoxycarbonylation or hydroxycarbonylation reactions has never been reported. An industrial process for methoxycarbonylation of the simple alkene, ethylene displays high reactivity (see W Clegg et al., *Chem. Commun.*, 1999, 1877). Catalysts are formed in situ, and both monomeric salts of type [Pd(P^P)dba] and Pd(P^P)Cl$_2$ (in which P^P represents a diphosphine) are used along with a tetrameric palladium compound was also isolated in mechanistic studies on these specific diphosphine ligands.

As is well known, it is of often of particular benefit to be able to produce more of one stereoisomer than another, in particular an optical isomer substantially free of its stereoisomers, where a target compound exhibits stereoisomerism. This benefit applies to hydrocarbonylation and hydroesterification reactions as much as any other reactions.

Classical methods of achieving differential amounts of stereoisomers have typically involved the separation of the stereoisomers, e.g. optically active isomers, from stereoisomeric, e.g. optically inactive (racemic), mixtures. However, such resolutions are often laborious, expensive and generate waste products. Owing to these difficulties, asymmetric synthetic methods have been developed in which optically active catalysts are used to carry out reactions in which an excess of one stereoisomer is produced.

Effective processes for the carbonylation of unsaturated compounds, and, which produce an excess of one optical isomer, are a key technology for the more efficient production of optically active carboxylic acids and esters. However, there is a continuing need for catalysts useful in such reactions that have good reactivity, stability and chemoselectivity.

Various hydroxycarbonylations and alkoxycarbonylations giving optically inactive products have been described. A. Seayad et al. (*Org. Lett.*, 1999, 1, 459-462) describe the hydroxycarbonylation of alkenes using palladium complexes of the triphenylphosphine in combination with lithium chloride and p-toluenesulfonic acid, typically used at 20 mol % relative to the alkene reactant. These processes were shown to afford good yields of optically inactive carboxylic acids at temperatures of around 115° C. Methoxycarbonylation of alkenes is generally understood to proceed under milder conditions than the analogous hydroxycarbonylation. H Ooka et al. (*Chem. Commun.*, 2005, 1173-1175) describe that Pd(OAc)$_2$ in combination with certain diphosphines combined in excess amounts relative to palladium can promote methoxycarbonylation of styrene at room temperature. C Godard et al. (*Helvetica Chim. Acta,* 2006, 89, 1610-1622) describe that temperatures of 100° C. are sufficient to achieve significant yields in methoxycarbonylation of styrene, although 150° C. was preferred. Although hydroxycarbonylation of styrene using diphosphines has never given high ratios of optical isomers (see I del Rio et al., infra), C Godard et al. describe ratios of the product esters of up to 92:8. E Guiu et al. (*Organometallics,* 2006, 25, 3102-3104) describe good yields in the same reaction at 90° C. although the ratio of optical isomers are not described as exceeding 70:30.

There are many examples in the art in which optionally optically active diphosphines chelated to single metal ions are used in various processes of asymmetric catalysis. However, there are very few reports that describe the asymmetric hydroxycarbonylation of alkenes. I del Rio et al, (*Eur. J. Inorg. Chem.*, 2001, 2001(11), 2719-2738) and H Alper & N Hamel (*J. Am. Chem. Soc.,* 1990, 112(7), 2803-2804) report high ratios of optical isomers upon the asymmetric hydroxycarbonylation of alkenes using catalysts formed from a simple palladium salt and a chiral phosphoric acid. Nevertheless, 10-20 mol % of the Pd catalyst is used, suggesting a low reactivity.

I del Rio et al. (infra) describe that moderate yields of modestly optically enriched carboxylic acids can be realised at 150° C. using optically active diphosphine ligands. However, the ratio of the optical isomers does not exceed 56:44 (an enantiomeric excess of 12%). The diphosphine palladium-containing catalysts comprise either isolated monomeric complexes of formula [Pd(P^P)X$_2$] (P^P is diphosphine; X is a halide), or are formed in situ with a palladium salt.

The processes described above bring useful technical knowledge, gradual improvement in performance and understanding, and include technology developed for two very specific applications: (methoxycarbonylation of ethylene and hydrocarbonylation of vinyl napthalenes in a racemic sense; methoxycarbonylation of ethylene does not require control over selectivity owing to the symmetry of ethylene, and the hydrocarbonylation of vinyl napthalenes in a racemic sense does not seek stereoselective control. However, there is an ongoing need for catalytic methods and catalysts more generally useful in the carbonylation of unsaturated compounds, and in particular in the hydroxycarbonylation, alkoxycarbonylation, aryloxycarbonylation or thiocarbonylation, e.g. hydroxycarbonylation and alkoxycarbonylation, of unsaturated compounds, that can preferably afford high stereospecificities in asymmetric reactions and/or with good yields of product. The present invention addresses this need in the art.

BRIEF DESCRIPTION OF THE FIGURE

FIG. 1 shows an X-ray structure of a complex of the invention ($[Pd_2((R)Xyl-Phanephos)Cl_4]$).

SUMMARY OF THE INVENTION

The present invention is based, in part, upon the surprising finding that [n,n']cyclophane-based ligands which are substituted once in each ring with a phosphorus atom-containing substituent may be used to catalyse hydroxycarbonylation and alkoxycarbonylation reactions, for example through the formation of complexes comprising one or two metal centres. Moreover, we have found that the use of such ligands advantageously allows stereoselective hydroxycarbonylation and alkoxyoxycarbonylation reactions to be effected to prochiral unsaturated molecules, in particular alkenes.

Additionally, the invention is not limited to the use of alcohols and water whereby to effect hydroxycarbonylation and alkoxycarbonylation reactions. Phenols and thiols may also be reacted analogously whereby to effect aryloxycarbonylation and thiocarbonylation reactions respectively.

Viewed from a first aspect, therefore, the invention provides a method for the hydroxycarbonylation, alkoxycarbonylation, aryloxycarbonylation or thiocarbonylation of an unsaturated molecule comprising effecting a hydroxycarbonylation, alkoxycarbonylation, aryloxycarbonylation or thiocarbonylation reaction on the unsaturated molecule in which a complex comprising a ligand comprising a [n,n']cyclophane comprising two non-fused monocyclic aromatic rings bridged by two linear and aliphatic linkages, in which each of the non-fused monocyclic aromatic rings is substituted with a phosphorus atom-containing substituent, is used to catalyse the hydroxycarbonylation, alkoxycarbonylation, aryloxycarbonylation or thiocarbonylation reaction.

Viewed from a second aspect, the invention provides the use of a ligand comprising a [n,n']cyclophane comprising two non-fused monocyclic aromatic rings bridged by two linear and aliphatic linkages, in which each of the non-fused monocyclic aromatic rings is substituted with a phosphorus atom-containing substituent, to catalyse a hydroxycarbonylation, alkoxycarbonylation, aryloxycarbonylation or thiocarbonylation reaction.

Dimeric complexes—i.e. complexes comprising two metal centres—that may be used in accordance with the first and second aspects of the invention, and in which one of the two phosphorus atoms is coordinated to each metal centre, have not been described hitherto and so constitute a further aspect of the present invention. Viewed from a third aspect, therefore, the invention provides a complex comprising two metal centres and a ligand comprising a [n,n']cyclophane comprising two non-fused monocyclic aromatic rings bridged by two linear and aliphatic linkages, in which each of the non-fused monocyclic aromatic rings is substituted with a phosphorus atom-containing substituent.

Still further, the invention is based upon the surprising finding that dimeric complexes that comprise a ligand having two phosphorus atoms, in which one of the phosphorus atoms is coordinated to each metal centre, have utility in the hydroxycarbonylation, alkoxycarbonylation, aryloxycarbonylation or thiocarbonylation, e.g. hydroxycarbonylation and alkoxycarbonylation, of unsaturated molecules. We have found that the use of such complexes advantageously allows stereoselective hydroxycarbonylation, alkoxycarbonylation, aryloxycarbonylation or thiocarbonylation, e.g. hydroxycarbonylation and alkoxycarbonylation, of prochiral unsaturated molecules, in particular alkenes, to be achieved.

Viewed from a fourth aspect, therefore, the invention provides a method for the hydroxycarbonylation, alkoxycarbonylation, aryloxycarbonylation or thiocarbonylation of an unsaturated molecule comprising effecting a hydroxycarbonylation, alkoxycarbonylation, aryloxycarbonylation or thiocarbonylation reaction on the unsaturated molecule in which a complex comprising two metal centres and a ligand comprising two phosphorus atoms is used to catalyse the hydroxycarbonylation, alkoxycarbonylation, aryloxycarbonylation or thiocarbonylation reaction.

Viewed from a fifth aspect, the invention provides the use of a complex comprising two metal centres and a ligand comprising two phosphorus atoms to catalyse the hydroxycarbonylation, alkoxycarbonylation aryloxycarbonylation or thiocarbonylation of an unsaturated molecule.

Particular embodiments of all aspects of the invention relate to hydroxycarbonylation, alkoxycarbonylation and aryloxycarbonylation reactions. Other particular embodiments of all aspects of the invention relate to hydroxycarbonylation, and alkoxycarbonylation reactions Further aspects and embodiments of the present invention will become apparent from the detailed discussion of the invention that follows below.

Detailed Description of the Invention

The expression "used to catalyse" herein indicates that a compound or complex qualified in this way may be used to promote a hydroxycarbonylation, alkoxycarbonylation, aryloxycarbonylation or thiocarbonylation reaction, e.g. a hydroxy- or alkoxycarbonylation reaction, in a substoichiometric amount (relative to the unsaturated compound). The expression does not require that the compound or complex is the actual catalytic species since, as is understood by those skilled in the art, the actual catalytic species may be formed in situ. Typical substoichiometric amounts will be in the range of about 0.0000001 to about 0.2 molar equivalents, e.g. about 0.00001 to about 0.2 molar equivalents, typically about 0.001 to about 0.02 molar equivalents, relative to the amount of unsaturated substrate.

It is also known in the art that many metal-containing complexes are converted during a reaction into a different complex that constitutes an intermediate in the catalytic cycle. It is to allow for this premise that the term "metal centre" is used herein: by this is meant a metal atom in either a neutral or cationic oxidation state.

Thus, for example, a complex comprising one or two metal ions may be added to a reaction medium. Alternatively, a metal complex may be added comprising metal atoms in oxidation state 0. Typically the complexes described herein comprise metal ions as the metal centres, typically in oxidation state +2 although metals in other oxidation states, e.g. Pd(I) and Pd(IV), may also be used in accordance with this invention. It will be understood that these and other complexes of the invention may be formed in situ or ex situ by combination of appropriate ligands (including a ligand having two phosphorus atoms) with metal (0) and/or ionic metal, e.g. metal(II), precursors. Examples of the latter include metal halide and acetate salts.

By ex situ is meant that a complex is made and introduced as such; by in situ is meant, for example, that a complex is made by adding suitable precursors such as metal complexes or salts and an appropriate ligand or ligands to a vessel in which a hydroxy- or alkoxycarbonylation is conducted.

Hereinafter, attention is directed primarily towards hydroxycarbonylation and alkoxycarbonylation reactions. However, the invention is not to be understood to be so limited. In particular, the skilled person is aware that the teachings herein may apply to thiocarbonylation reactions by use of a thiol in place of the alcohol used when effecting a alkoxycarbonylation reaction; and to aryloxycarbonylation reactions by use of an aromatic alcohol, typically a monocyclic non-heteroaromatic alcohol, such as an optionally substituted phenol, in place of the alcohol used when effecting a alkoxycarbonylation reaction.

As used herein the term "halide" refers to fluoride, chloride, bromide or iodide, typically chloride, bromide or iodide.

As used herein the term aromatic embraces within its scope heteroaromatic. As known to those skilled in the art, heteroaromatic moieties are a subset of aromatic moieties that comprise one or more heteroatoms, typically O, N or S, in place of one or more carbon atoms and any hydrogen atoms attached thereto. Such exemplary heteroaromatic moieties, for example, include pyridine, furan, pyrrole and pyrimidine.

Aromatic moieties may be polycyclic, i.e. comprising two or more fused aromatic (including heteroaromatic) rings. Naphthalene and anthracene are examples of polycyclic aromatic moieties, and benzimidazole is an example of a polycyclic heteroaromatic moiety.

Aromatic moieties, including aryl and arylene radicals and diradicals (formed formally by abstraction of one or two hydrogen atoms from an aromatic moiety) may be optionally substituted with one or more substituents selected from halo (e.g. fluoro, chloro, bromo and iodo), alkyl, aryl (including heteroaryl), hydroxy, nitro, amino, alkoxy, alkylthio, carboxy, cyano, thio, formyl, ester, acyl, thioacyl, amido, carbamido and sulfonamide.

By alkyl is meant herein a saturated hydrocarbyl moiety, which may be straight-chain, cyclic or branched (typically straight-chain unless the context dictates to the contrary). By alkylene is meant an alkyl group from which a hydrogen atom has been formally abstracted. Typically alkyl and alkylene groups will comprise from 1 to 25 carbon atoms, more usually 1 to 10 carbon atoms, more usually still 1 to 6 carbon atoms. Alkyl and alkylene groups may be substituted, for example once, twice, or three times, e.g. once, i.e. formally replacing one or more hydrogen atoms of the group.

Examples of such substituents are halo (e.g. fluoro, chloro, bromo and iodo), aryl, heteroaryl, hydroxy, nitro, amino, alkoxy, alkylthio, carboxy, cyano, thio, formyl, ester, acyl, thioacyl, amido, carbamido, sulfonamido and the like. Examples of aryl (e.g. heteroaryl) substituted alkyl (i.e. aralkyl (e.g. heteroaralkyl)) include $CH_2$-aryl (e.g. benzyl) and $CH_2$-heteroaryl.

By carboxy is meant herein the functional group $CO_2H$, which may be in deprotonated form ($CO_2^-$).

By acyl and thioacyl are meant the functional groups of formulae —C(O)-alkyl or —C(S)-alkyl respectively, where alkyl is as defined hereinbefore.

By amido is meant a functional group comprising the moiety —N(H)C(=O)—;

By carbamido is meant a functional group comprising the moiety —N(H)C(=O)—;

By ester is meant a functional group comprising the moiety —OC(=O)—;

By sulfonamido is meant a functional group comprising the moiety —$SO_2$N(H)$_2$— in which each hydrogen atom depicted may be replaced (independently in sulfonamido) with alkyl or aryl.

Alkyloxy (synonymous with alkoxy) and alkylthio moieties are of the formulae —O-alkyl and —S-alkyl respectively, where alkyl is as defined hereinbefore.

Alkylamino and dialkylamino moieties are of the formulae —N(H)-alkyl and

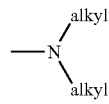

respectively, where alkyl is as defined hereinbefore.

By amino group is meant herein a group of the formula —N($R^x$)$_2$ in which each $R^x$ is independently hydrogen, alkyl or aryl, e.g. an unsaturated, unsubstituted $C_{1-6}$ alkyl such as methyl or ethyl, or in which the two $R^x$s attached to the nitrogen atom N are connected. One example of this is whereby —$R^x$—$R^x$— forms an alkylene diradical, derived formally from an alkane from which two hydrogen atoms have been abstracted, typically from terminal carbon atoms, whereby to form a ring together with the nitrogen atom of the amine. As is known the diradical in cyclic amines need not necessarily be alkylene: morpholine (in which —$R^{-Rx}$— is —(CH$_2$)$_2$O(CH$_2$)$_2$—) is one such example from which a cyclic amino substituent may be substituted, may be prepared.

References to amino herein are also to be understood as embracing within their ambit quaternised or protonated derivatives of the amines resultant from compounds comprising such amino groups. Examples of the latter may be understood to be salts such as hydrochloride salts.

The ligands present in all the complexes described herein function as bidentate ligands, that is to say they are capable of coordinating through two discrete donor sites within the phosphorus-containing ligand, namely the two phosphorus atoms. The invention does not exclude the possibility that these ligands have denticity of greater than two, that is to say have structures capable of coordinating through more than two donor sites. In most embodiments of the invention, however, the ligands will coordinate to the metal centre(s) present in the complexes described herein through only their two phosphorus atoms.

In accordance with the present invention, ligands may be based upon a [n,n']cyclophane. [n,n']cyclophane is a term of the art used to indicate that the compound is a member of a specific class of cyclophanes defined by having two aromatic rings joined by linking moieties having n and n' atoms in their respective backbones. In this way the use of the [n,n'] prefix distinguishes over other cyclophanes, such as [n]para- and [n]metacyclophane in which two atoms of one aromatic ring are connected to each other by a linking moiety having n atoms in its backbone.

At one time, the term [n,n']cyclophane referred to compounds having two para-disubstituted benzene rings held face to face by linkages through two (CH$_2$)$_n$ linkages. With the passage of time and through the development of chemistry it has now acquired a generally broader construction and by [n,n']cyclophane is meant herein a compound comprising two non-fused monocylic aromatic rings, typically having six ring atoms, with two linkages, which are typically linear and aliphatic, bridging the two rings, in which one of the linkages comprises n atoms in its backbone and the other linkage comprises n' atoms in its backbone. It is each of these two non-fused monocylic aromatic rings that are substituted by a phosphorus atom-containing substituent in the ligands that comprise a [n,n']cyclophane defined according to the first to third aspects of the invention.

Typically but not necessarily, the non-fused monocylic aromatic rings are not heteroaromatic, i.e. are para-disubstituted phenylene rings. Typically n and n' are between 2 and 4. Typically n and n' are the same. Thus the linkages may be, for example, ethylene (—CH$_2$CH$_2$—), n-propylene (—CH$_2$CH$_2$CH$_2$—) or n-butylene (—CH$_2$CH$_2$CH$_2$CH$_2$—). Whilst the linkages are typically aliphatic hydrocarbyl linkages, one or more, e.g. one, of the methylene units (—CH$_2$—) in such aliphatic hydrocarbyl linkages may be exchanged for a heteroatom-containing moietiy, such as —O—, —S—, —SO—, —SO$_2$— or —NH—, optionally in which the hydrogen atom depicted in —NH— is exchanged for an alkyl group, e.g. a C$_{1-6}$ alkyl group. Often each of the two linkages are the same and are ethylene, n-propylene or n-butylene, typically ethylene.

Typically [n,n']cyclophanes are based on para-disubstituted arylene rings; these are referred to herein as [n,n']paracyclophanes, it to be understood that reference to paracyclophanes indicates the presence of two para-disubstituted phenylene or heteroarylene rings. In many embodiments of the invention, the [n,n']paracyclophanes are bis(alkylene)-bridged, in which each of n and n' represents an alkylene group, typically comprising between 2 and 4 carbon atoms, e.g. ethylene, n-propylene or n-butylene. In many embodiments of the invention the paracyclophanes described herein are [n,n']para(phenylene)cyclophanes, i.e. [n,n']paracyclophanes based on two para-disubstituted phenylene moieties. In particular embodiments, n and n' in the [n,n']para(phenylene)cyclophanes described herein each represent an alkylene group, typically comprising between 2 and 4 carbon atoms, e.g. ethylene, n-propylene or n-butylene.

In all embodiments of the invention, the non-fused monocyclic aromatic rings of the [n,n']cyclophane may be independently substituted, additionally to the linear aliphatic bridging linkages that is, by one or more additional substituents. Access to such compounds may be readily achieved by the skilled person. For example, formyl-, acyl-, ester- carboxy-, alkoxy- and hydroxymethyl-substituted [n,n']cyclophanes, including [2,2']para(phenylene)cyclophanes, are described by B Dominguez et al., *Org. Lett.*, 2004, 6(12), 1927-1930.

The most studied [n,n']cyclophanes are arguably the [n,n']para(phenylene)cyclophanes in which n and n' are each ethylene. Such compounds are referred to herein as [2,2']para(phenylene)cyclophanes—i.e. in which the [2,2'] prefix specifically denotes the presence of two ethylene bridges. Sometimes, in the art, the specific reference in "[2,2']para(phenylene)cyclophane" to the two arylene groups being based on phenylene is omitted and such compounds are referred to as [2,2']paracyclophanes. The subsequent discussion focuses on this archetypal subset of the [n,n']cyclophane class of compounds—i.e. comprising two substituted phenylene rings bridged to each other through two ethylene linkages—although the invention is not to be understood to be so limited.

In accordance with the present invention, where ligands comprise [n,n']cyclophanes substituted with two phosphorus atoms, these may be prepared by methods known in the art, for example by preparing a dibrominated [2,2']para(phenylene)cyclophane (with one bromo substituent in each of the phenylene rings) as described by H J Reich and D J Cram (*J. Am. Chem. Soc.*, 1969, 91(13), 3527-3533). Dibrominated [2,2']para(phenylene)cyclophanes in particular allow access to a wide spectrum of [2,2']para(phenylene)cyclophanes bearing a phosphorus-containing substituent in each ring. Examples are described in WO 97/47632, WO 02/05728 and WO 2004/111065, for example.

Additionally or alternatively such ligands may also possess structural features of the type described in WO 02/057278, in which the development of ps-ortho bis(diphosphino)[2,2'] para(phenylene)cyclophanes (i.e. [2,2']para(phenylene)cyclophanes substituted with unsubstituted phosphino (—PH$_2$) subsituents in the ps-ortho (i.e. 4 and 12) positions) allowed the preparation of phosphorus-containing ps-ortho disubsutituted [2,2']para(phenylene)cyclophanes other than diphosphine derivatives (e.g. phosphonite, phosphorus amide and phosphonamidite ps-ortho disubsututited [2,2']para(phenylene)cyclophanes) by, for example, following the teachings of A Zanotti-Gerosa et al. (Org. Lett., 2001, 3(23), 3687-3690; see also WO 2004/111065). Alternatively, the valences of either phosphorus atom not involved in bonding to the [n,n'] cyclophane structure can be incorporated into a cyclic structure such as a phosphetane, phospholane or phosphinane that can be optically active or inactive.

Additionally or alternatively such ligands may also possess structural features of the type described in WO 2004/111065, in which the provision of phosphorus-containing ps-ortho disubsututited [2,2']para(phenylene)cyclophanes containing substitution in the phenylene rings of the [2,2']para(phenylene)cyclophane motif is described. As described in this publication, the presence of such additional functionalisation provides an additional way in which the ligand may be optimised (e.g. for activity or selectivity) for use in any given reaction and/or to allow facile immobilisation of such ligands, or complexes comprising such ligands, to solid supports whereby to allow use in a heterogeneous system.

A particular advantage of the present invention is the finding that, where the complexes used in accordance with the present invention comprise a chiral [n,n']cyclophane in which each ring comprises a phosphorus atom-containing substituent, improved stereoselectivity may be achieved in hydroxycarbonylations or alkoxycarbonylations effected upon alkenes in which stereogenic centres are generated upon hydroxycarbonylation or alkoxycarbonylation.

Chiral [n,n']cyclophane-containing ligands substituted with two phosphorus atoms are known in the art. A particular class that we have found to be effective are the so-called pseudo-ortho (ps-ortho) disubsutituted paracyclophanes with the ps-ortho disubstitution being by phosphorus-containing moieties, usually (but not necessarily) phosphines. This class of compounds was first described by P J Pye et al. (*J. Am. Chem. Soc.*, 1997, 119(26), 6207-6208 and in WO 97/47632) and exemplified with ps-ortho disubstituted [2,2']para(phenylene)cyclophanes. In these ps-ortho disubsutituted [2,2'] para(phenylene)cyclophanes two, typically identical, phosphorus-containing substituents are present at the 4- and 12-positions of [2,2']para(phenylene)cyclophane. Consequentially such compounds exhibit planar chirality but, whilst their use in catalysing a number of asymmetric reactions has been described, there is no mention of the utility of either these ligands, in any asymmetric hydroxycarbonylation, alkoxycarbonylation, aryloxycarbonylation or thiocarbonylation reaction, e.g. in a hydroxycarbonylation or alkoxycarbonylation reaction.

Particular embodiments of the present invention involve use of a chiral ps-ortho disubsutituted paracyclophane, particularly a ps-ortho disubstituted [2,2']para(phenylene)cyclophane. Such chiral [2,2']paracyclophanes may be prepared in accordance with the teachings of inter alia Pye et al. (infra), WO 02/052728, and WO 2004/111065 and examples are now commercially available, including (R)-(−)-4,12-bis-(diphenylphosphino)-[2,2']paracyclophane, (S)-(+)-4,12-bis-(diphenylphosphino)-[2,2']paracyclophane, (R)-(−)-4,12-bis-(di(3,5-xylyl)Iphosphino)-[2,2']paracyclophane and (S)-(+)-4,12-bis-(di(3,5-xylyl)Iphosphino)-[2,2'] paracyclophane, which may be purchased from Aldrich. 4,12-bis-(diphenylphosphino)-[2,2']paracyclophane, (which is the same racemate as ps-ortho bis(diphenylphosphino) [2,2'] paracyclophane) is often referred to in the art as PHANEPHOS.

There is no particular limitation on the nature of the optionally chiral ps-ortho disubsutituted (optionally [2,2']) paracyclophanes (e.g. chiral ps-ortho disubsutituted (optionally [2,2']) para(phenylene)cyclophanes) that may be used in accordance with the present invention. Thus these may be the archetypal chiral ps-ortho bis(phosphino) para(phenylene) cyclophanes described by P J Pye et al. (infra), typically ps-ortho bis(diarylphosphino)[n,n']para(phenylene)cyclophanes (in which n and n' are independently selected from but typically dependently selected from 2, 3 and 4, and are each typically 2; and/or the aryl groups of the phosphines are typically the same, non-heteroaromatic and optionally substituted one or more times, e.g. with methyl, alkoxy (e.g.) methoxy, halo (e.g. fluoro) or haloalkyl (including trihalomethyl (e.g. trifluoromethyl)). For example, where phosphino groups are present on each of the monocyclic aryl groups of the [n,n']cyclophanes, e.g. [2,2']para(phenylene)cyclophanes, these may be di(3,5-bis-trifluoromethylphenyl)phosphino groups.

The chiral ps-ortho disubsutituted paracyclophanes may also comprise the structural features described in WO 02/57278 and WO 2004/111065 as discussed above.

The [n,n']cyclophanes used according to the first and second aspects of the invention may involve the formation of either a monomeric or dimeric complex, i.e. comprising one or two metal centres. Whilst many embodiments of the present invention are based on the use of dimeric complexs, embodiments of the present invention also embrace the use of monomeric complexes comprising a ligand comprising a [n,n']cyclophane substituted in each ring with a phosphorus atom-containing substituent chelated to one metal centre. Synthesis of a monomeric or dimeric complex may be achieved by control over the stoichiometry of metal:ligand ratio, whether the complexes are made ex or in situ.

In accordance with the second aspect of the invention the ligand need not be used in an amount stoichiometrically tailored to form a monomeric or a dimeric complex—the ratio of ligand to metal can be in the range of about 0.1:1 to 10:1, typically in the range of about 0.5:1 to 1:1, a stoichiometry of 0.5 to 1 being that which is found in the dimeric complexes described herein. The complexes used according to the present invention can be prepared according to the normal skill of those of skill in the art typically by contacting a suitable ligand comprising two phosphorus atoms, e.g. a [pn, n']cyclophane-based ligand, and a source of metal, typically a metal (II) salt or salts in the appropriate stoichiometric ratio in a suitable solvent (typically degassed) and typically under an inert atmosphere. Examples are provided below.

The metal centres in the complexes will typically be transition metals. Where a complex comprises one metal centre, this will typically be a Group 10 transition metal, typically palladium, platinum or nickel, most usually palladium. Where a complex comprises two metal centres, one metal centre will typically be a Group 10 transition metal, typically palladium, platinum or nickel, most usually palladium. The other metal centre may be of any of the following: Pd, Pt, Ni, Rh, Ir, Co, Cu, Zn, Fe, Os, Re, Tc, Mn and Ru, often Pd, Pt, Ni. In some embodiments of the dimeric complexes of the invention both metal centres are palladium.

The dimeric complexes of or used according to the third to fifth aspects of the invention each comprise a ligand comprising two phosphorus atoms that serves as a bridging ligand between the two metal centres in the complexes that are used to catalyse the hydroxycarbonylation, alkoxycarbonylation, aryloxycarbonylation or thiocarbonylation reactions, e.g. hydroxycarbonylation or a alkoxycarbonylation reactions.

As is known in the art a bridging ligand is a ligand that coordinates to two or more atoms, typically metal atoms. In the complexes according to these aspects of the invention, the phosphorus-containing ligand does not serve to chelate the metal centres, since, as is also known in the art, chelation requires that the formation or presence of coordination between two or more separate binding sites within the same ligand and a single atom.

There is no particular limitation on the phosphorus-containing ligands that are used to make the dimeric catalysts used in accordance with particular aspects of the present invention, provided that they are capable of forming the desired dimeric complex. Such complexes are unusual, but not unprecedented, in the art.

An example of complexes in which a diphosphine ligand bridges two metal atoms is described by A El-Qissairi and P M Henry (*J. Organomet. Chem.*, 2000, 603, 50-60). The authors suggest that diphosphine or diamino ligands can be made to bridge two palladium centres, with the assistance of a triketone ligand that is designed to favour the formation of bridges between two metals, although limited evidence of the catalysts structure was provided. Such complexes are described as being of use in chlorohydrin formation.

O Grossman et al. (*Organometallics*, 2006, 25, 375-381) describe that if the backbone of a diphosphine ligand is constructed so that the phosphorus atoms are disposed at an appropriate distance from each other, it is possible to form palladium-containing dimers of type $[Pd_2Cl_4(P\widehat{\ }P)_1]$ directly in which the diphosphine ligand $(P\widehat{\ }P)$ bridges two palladium centres. Further studies from the same group are reported in Inorganic Chemistry (2006, 45, 7010-7017).

Whilst there are no reports of the use of dimeric complexes being used in any form of carbonylation reaction, therefore, such complexes are known in the art and the relevant considerations in designing or selecting appropriate bridging bidentate phosphorus-containing ligands are at the disposal of those skilled in the art. Typical considerations include the selection of ligands with a relatively large bite angles (i.e. generally greater than 95° and typically having a bite angle of between 95 and 135°, e.g. about 99 to about 120°); and/or in which the distance between the phosphorus atoms is sufficiently great to allow the formation of the desired dimeric complexes. The concept of bite angle is one with which the skilled person is familiar, diphosphines with wide bite angles being described for example by P C J Kamer et al. (*Acc. Chem. Res.*, 2001, 34, 895-904).

It will be apparent to those of skill in the art, therefore, from the teachings herein and in the prior art (e.g. by O Grossman et al., infra) that ligands containing two phosphorus atoms are known that can stretch to place their phosphorus atoms more than 4.8 Å apart, (as determined by molecular mechanics calculations on a hypothetical ligand structure using programmes, datasets and assumptions typical to those skilled in the art, or X-ray crystal structures of dimeric complexes in the solid state) may be suitable for forming dimeric complexes of use in the invention described herein.

The dimeric catalysts used in or according to the various aspects of the present invention are typically of the formula (I)

[M$^1$M$^2$(μ-X)$_2$(X)$_2$(μ-P^P)$_1$] (I)

wherein:

M$^1$ is a Group 10 transition metal, typically palladium, platinum or nickel, most typically palladium;

M$^2$ is a transition metal, typically palladium, platinum or nickel, most typically palladium;

each X is independently an anionic ligand that can adopt both bridging or terminal co-ordination modes; and P^P is a ligand containing two phosphorus atoms that binds to both M$^1$ and M$^2$.

As will be understood by those of normal skill in the art, in reciting the formula of a complex in which a ligand bridges two metal centres, as in the dimeric complexes of the present invention, and in particular of formula (I) above, the bridging ligand is preceded by the symbol p. Whilst a superscripted number may denote the number of metal centres to which such a bridging ligand is bound, convention dictates that μ$^2$ is often denoted simply as μ. That conventon is adopted herein.

Whilst transition metal M$^1$ is typically a Group 10 transition metal, typically palladium, platinum or nickel, most typically palladium, the nature of M$^2$ is not so limited. It is known to those of normal skill in the art of co-ordination chemistry that complexes with very similar chemical properties and structures result when a transition metal centre within a complex is substituted for another transition metal centre. Thus M$^2$ may be a metal centre of any of the following: Pd, Pt, Ni, Rh, Ir, Co, Cu, Zn, Fe, Os, Re, Tc, Mn and Ru. In some embodiments of the invention, M$^2$ is a Pd, Pt or Ni metal centre. In other embodiments of the invention, M$^2$ is a Pd or Pt metal centre. In further embodiments of the invention, M$^2$ is a Pd metal centre. Typically M$^1$ and M$^2$ will be the same.

Each X is an anionic ligand that can adopt both bridging or terminal co-ordination modes. These include halide, carboxylate, phosphonate, sulfonate, amido, ketonate, alkoxy, hydroxy, phosphido, and thiolate ligands. Typically each X ligand is a halide, e.g. chloride, bromide or iodide, for example chloride or bromide, e.g. chloride. Typically the non-bridging X ligands will be the same and the bridging (μ-X) X ligands will be the same. In some embodiments, all X ligands will be the same. Where complexes used according to this invention, including dimeric catalysts of formula (I), are formed in situ, in situ formation may be achieved by, for example, contact of salts of a suitable cation, such as a metal or ammonium ion, and a ligand (e.g. a bridging ligand) such as a halide (e.g. chloride), sulfide, alkoxide, phosphide, phosphate, carboxylate or other suitable ligand.

The P^P ligands used according to this invention comprise a linking moiety between the phosphorus atoms that allows for them to be sufficiently separated in the desired dimeric complex. Typically, but not necessarily, this linking moiety will comprise one or more optionally substituted aromatic moieties interposed between the phosphorus atoms with additional carbon or other atoms present in the structure. The linking moiety may be constituted by a hydrocarbyl chain, optionally (but typically not) interrupted by one or more heteroatoms such as oxygen, sulfur and nitrogen. The length of such a chain will be selected, generally though routine optimisation, so as to construct an appropriate ligand from which a dimeric complex that may be used according to the invention can be made. Such considerations do not present the skilled person with any difficulty since the correlation between the linking moiety in ligands containing two phosphorus atoms, particularly diphosphines, and the size of macrocylic ring that may thereby be formed upon coordination, including chelation, to metal centres is well-documented (see, for example, F A Cotton and G Wilkinson, *Advanced Inorganic Chemistry*, 5th ed.; Wiley-Interscience: New York, N.Y., 1988; pp 434 to 436 and references cited therein).

Typically, the backbone of the linking moiety connecting the two phosphorus atoms consists of three to ten atoms, typically carbon atoms, although the phosphorus atoms may be directly attached to a heteroatom, e.g. an oxygen atom or nitrogen atom in the backbone. As an illustration of this nomenclature, the backbone of the linking moiety in 1,4-bis (diphenylphosphino)butane (dppb)-butylene—has four atoms.

In addition to the linking moiety between the phosphorus atoms in the P^P ligand, the phosphorus atoms bear additional substituents. In many embodiments of the invention the phosphorus-containing ligands are bidentate phosphines, in particular in which each of the phosphorus atoms is substituted with organic groups such as optionally substituted alkyl or aryl moieties. Typically all four of the moieties with which such phosphines are substituted, (i.e. apart from the linking moiety that is) will be the same. Typically they will be optionally substituted aryl groups and often optionally substituted phenyl groups, for example phenyl or alkyl-substituted phenyl.

In alternative embodiments of the invention bidentate phosphorus-containing ligands other than diphosphines can be used. For example, bidentate diphosphonite ligands such as those described by M T Reetz et al. (*Chem. Commun.*, 1998, 2077-2078), WO 00/14096 and U.S. Pat. No. 5,817, 850; bidentate phosphine-phosphonite ligands such as those described by M T Reetz and A Gosberg (*Tetrahedron: Asymmetry*, 1999, 10(11), 2129-2137); or bidentate phosphoramidites (monodentate phosphoramidites are described by A J Minaard et al. (*Acc. Chem. Res.*, 2007, 40(12), 1267-1277)) may be used instead of bidentate phosphines.

A number of ligands comprising the two phosphorus atoms (P^P ligands) are known in the art from which the dimeric complexes of and/or used in accordance with the present invention may be prepared. By way of example, suitable P^P ligands will now be described.

According to particular embodiments of the invention, the P^P ligands may be any ligand comprising a [n,n']cyclophane substituted once in each ring with a phosphorus atom-containing substituent as described in detail above.

Alternatively, the P^P ligands may be diphosphines derived from axially chiral diols and diamines (whether the chiral axis is configuration stable or not), typically having any of the general formulae:

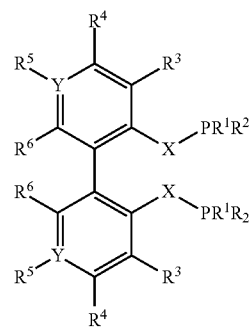

-continued

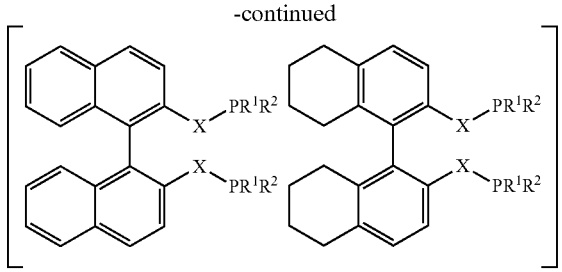

(wherein
X is O, NR (wherein R is hydrogen or an alkyl or aryl group), or CH$_2$;
Y is carbon or nitrogen;
each R$^1$ to R$^6$ are independently selected from hydrogen, or an alkyl or aryl group bound to the atom shown by either carbon, nitrogen or oxygen, and can be chiral or achiral, or two or more adjacent R$^3$ to R$^6$ together form a fused ring aromatic or non-aromatic ring (as depicted by way of the binaphthyl- and octahydrobinaphthyl-containing compounds depicted in square brackets above);
R$^1$ and R$^2$ can be the same groups or different, and in the latter case can create a chiral centre on the phosphorus atom that may be optically pure or racemic and may optionally be part of a cyclic structure, commonly known as the phospetanes, phospholanes or phosphinanes that can be chiral or achiral).

It is known that modification of the substituents within this general structure can adjust performance, but does not change the essential properties of the ligand, in particular those that make it suitable for forming the dimeric complexes used according to the various aspects of the present invention. Examples of such compounds are described by Y-G Zhou at al. (*J. Am. Chem. Soc.*, 2002, 124, 4952-53 and references therein); F-Y Zhang at al. (*J. Am. Chem. Soc.*, 1998, 120, 5808-9 and references therein); C P Casey et al. (*J. Am. Chem. Soc.*, 1992, 114, 5535-5543); W A Herrmann et al. (*Organometallics* 1996, 14(4), 1961-8).

Alternatively, the P^P ligands may be ferrocenes or ruthenocenes of general formula:

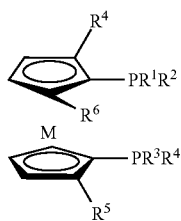

(wherein:
M is Fe or Ru;
R$^1$ to R$^6$ are independently selected from hydrogen, or an alkyl or aryl group bound to the atom shown by either carbon, nitrogen or oxygen, and can be chiral or achiral;
R$^1$-R$^4$ can be the same groups or different, and in the latter case can create a chiral centre on the phosphorus atom that may be optically pure or racemic, and R$^1$ and R$^2$ and/or R$^3$ and R$^4$ can be part of a cyclic structure, for example, those commonly known as the phosphetanes, phospholanes or phosphinanes that can be chiral or achiral).

It is known that modification of the substituents within this general structure can adjust performance, but does not change the essential properties of the ligand, in particular those that make it suitable for forming the dimeric complexes used according to the various aspects of the present invention.

Alternatively, the P^P ligands may be an enantiomerically pure or racemic member of the 'SPANPHOS' family of ligands having a typical formula:

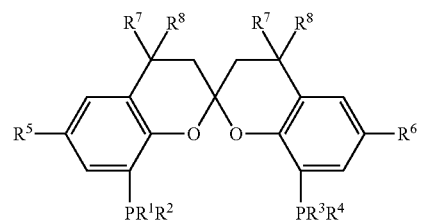

(wherein:
R$^1$ to R$^8$ are independently selected from hydrogen, or an alkyl or aryl group bound to the atom shown by either carbon, nitrogen or oxygen, and can be chiral or achiral;
R$^1$-R$^4$ can be the same groups or different, and in the latter case can create a chiral centre on the phosphorus atom that may be optically pure or racemic, and R$^1$ and R$^2$ and/or R$^3$ and R$^4$ can be part of a cyclic structure, for example, those commonly known as the phosphetanes, phospholanes or phosphinanes that can be chiral or achiral).

It is known that modification of the substituents within this general structure can adjust performance, but does not change the essential properties of the ligand, in particular those that make it suitable for forming the dimeric complexes used according to the various aspects of the present invention. Examples of such compounds are described by Z Freixa et al. (*Angew. Chem. Int. Ed,* 2005, 44, 4385-4388).

Alternatively, the P^P ligands may be a so-called XANTPHOS and DPE-phos derivatives of general structure shown below.

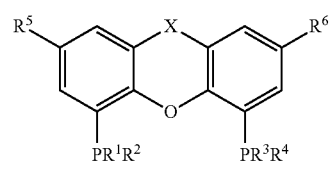

XANTPHOS family

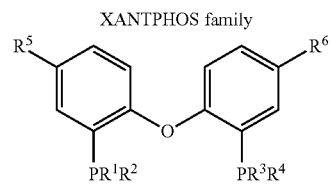

DPEPHOS family (wherein:
X is O, SiR$^7$R$^8$, NR$^9$, CR$^{10}$R$^{11}$;
R$^1$ to R$^{11}$ are independently selected from hydrogen, or an alkyl or aryl group bound to the atom shown by either carbon, nitrogen or oxygen, and can be chiral or achiral;
R$^1$-R$^4$ can be the same groups or different, and in the latter case can create a chiral centre on the phosphorus atom that may be optically pure or racemic, and R$^1$ and R$^2$ and/or R$^3$ and R$^4$ can be part of a cyclic structure, for example, those commonly known as the phosphetanes, phospholanes or phosphinanes that can be chiral or achiral).

It is known that modification of the substituents within this general structure can adjust performance, but does not change the essential properties of the ligand, in particular those that make it suitable for forming the dimeric complexes used according to the various aspects of the present invention. Examples of such compounds are described by L A van der Veen et al. (Organometallics 1999, 18, 4765-77 and references therein).

Alternatively, the P^P ligands may be an enantiomerically pure or racemic diphosphine of the so-called 'TRAP' family with the general structure shown below:

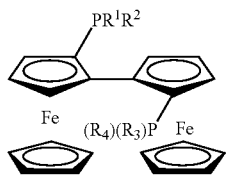

(wherein:
$R^1$ to $R^4$ are independently selected from hydrogen, or an alkyl or aryl group bound to the atom shown by either carbon, nitrogen or oxygen, and can be chiral or achiral;
$R^1$-$R^4$ can be the same groups or different, and in the latter case can create a chiral centre on the phosphorus atom that may be optically pure or racemic, and $R^1$ and $R^2$ and/or $R^3$ and $R^4$ can be part of a cyclic structure, for example, those commonly known as the phosphetanes, phospholanes or phosphinanes that can be chiral or achiral).

It is known that modification of the substituents within this general structure can adjust performance, but does not change the essential properties of the ligand, in particular those that make it suitable for forming the dimeric complexes used according to the various aspects of the present invention. Examples of such compounds are described by M Sawamura et al. (*Tetrahedron: Asymmetry*, 1991, 2, 593-596).

Alternatively, the P^P ligands may be an enantiomerically pure or racemic diphosphine of the so-called Taniaphos family with general structure below:

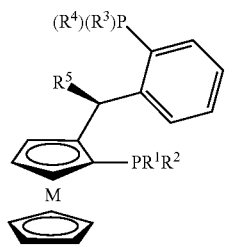

(wherein:
$R^1$ to $R^5$ are independently selected from hydrogen, or an alkyl or aryl group bound to the atom shown by either carbon, nitrogen or oxygen, and can be chiral or achiral;
$R^1$-$R^4$ can be the same groups or different, and in the latter case can create a chiral centre on the phosphorus atom that may be optically pure or racemic, and $R^1$ and $R^2$ and/or $R^3$ and $R^4$ can be part of a cyclic structure, for example, those commonly known as the phosphetanes, phospholanes or phosphinanes that can be chiral or achiral).

It is known that modification of the substituents within this general structure can adjust performance, but does not change the essential properties of the ligand, in particular those that make it suitable for forming the dimeric complexes used according to the various aspects of the present invention. Examples of such compounds are described by T Ireland et al. (*Chem. Euro J.* 2002, 8(4), 843-852).

Alternatively, the P^P ligands may be an enantiomerically pure or racemic spiro-phosphinites of general structure shown below:

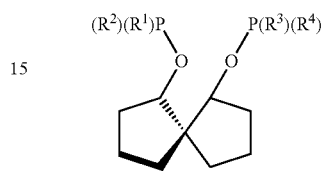

(wherein:
$R^1$ to $R^4$ are independently selected from hydrogen, or an alkyl or aryl group bound to the atom shown by either carbon, nitrogen or oxygen, and can be chiral or achiral; and, if different can create a chiral centre on the phosphorus atom that may be optically pure or racemic, and $R^1$ and $R^2$ and/or $R^3$ and $R^4$ can be part of a cyclic structure, for example, those commonly known as the phosphetanes, phospholanes or phosphinanes that can be chiral or achiral).

It is known that modification of the substituents within this general structure can adjust performance, but does not change the essential properties of the ligand, in particular those that make it suitable for forming the dimeric complexes used according to the various aspects of the present invention. Examples of such compounds are described by A S C Chan et al. (*J. Am. Chem. Soc.*, 1997, 119, 9570-9571).

A particular advantage of the present invention is the finding that, where the dimeric complexes used in accordance with the present invention comprise a chiral ligand that comprises two phosphorus atoms, improved stereoselectivity may be achieved in hydroxycarbonylations or alkoxycarbonylations effected upon alkenes in which stereogenic centres are generated upon hydroxycarbonylation or alkoxycarbonylation.

The invention relates in part to the catalysis of the hydroxycarbonylation and alkoxycarbonylation of unsaturated molecules. Hydroxycarbonylation and alkoxycarbonylation are well known reactions to chemists and involve addition to the unsaturated molecule of carbon monoxide and either water in the case of hydroxycarbonylation, or an alcohol in the case of alkoxycarbonylation. These reactions may be contrasted with hydroformylation in which hydrogen and a formyl group are added to an unsaturated molecule.

In certain embodiments of the invention the unsaturated molecule that is hydroxy- or alkoxycarbonylated is an alkene although it will be known to those in the art that the substrate may alternatively be an alkyne. In the discussion that follows, emphasis is placed upon the hydroxy- or alkoxycarbonylation of alkenes although it will be understood that the invention is not so limited and the description that follows applies mutatis mutandis to alkynic substrates.

There is no particular limitation to the nature of the alkene that may be hydroxy- or alkoxycarbonylated in accordance with the present invention. The alkene may be a terminal alkene (i.e. comprising a $H_2C=C$ moiety) or may be an internal alkene (i.e. comprising a $HC=CH$ moiety with neither of the remaining substituents being hydrogen). Internal alkenes thus include cyclic alkenes, e.g. norbornene or acyclic alkenes (e.g. stilbene). Terminal alkenes include alkenes comprising an $H_2C=C$ moiety with neither of the remaining substitutents being hydrogen.

A. Seayad et al. (infra) describe the hydroxycarbonylation of a number of alkenes, and lead one skilled in the art to conclude that a catalyst capable of efficient hydroxycarbonylation of styrene should have applicability in the hydroxy- and alkoxycarbonylation of many other substrates, including aryl- and alkyl-substituted alkenes. A. Rucklidge et al. (*Chem Commun.*, 2005, 1176) and B. Zhu et al. (*Appl. Organomet. Chem.*, 2006, 20, 277) describe that oxygen and nitrogen substituents directly bound to the alkene carbon do not impede alkoxycarbonylation reactions.

Although there is no particular limitation to the alkenes that may be hydroxy- or alkoxycarbonylated, these are in some embodiments of the invention of the general formula $R^1R^2CH=CH_2$ wherein $R^1$ and $R^2$ are each independently hydrogen an optionally substituted alkyl group, an optionally substituted aromatic group; or may comprise a nitrogen atom directly bound in the carbon atom depicted, whereby the alkene represents an enamide or an enamine, or may comprise an oxygen atom directly bound in the carbon atom depicted, whereby the alkene represents an enol ether. Alternatively the alkenes may be of the formula $R^1CH=CHR^2$ (wherein each of $R^1$ and $R^2$ are independently selected from the possibilities immediately hereinbefore defined for $R^1$) or of the formula $R^1CH=CR^2R^3$ (wherein each of $R^{1-3}$ are independently selected from the same possibilities immediately hereinbefore defined for $R^1$)

In certain embodiments of the invention the unsaturated substrate is ethylene.

Where the unsaturated molecule is an alkyne this may be of formula $R^1-C\equiv C-R^2$ wherein $R^1$ and $R^2$ are each independently hydrogen an optionally substituted alkyl group, an optionally substituted aromatic group; or may comprise a nitrogen atom directly bound in the carbon atom depicted whereby the alkyne represents an ynamide or an ynamine. In certain embodiments of the invention, the substrate is acetylene.

As will be understood from the preceding discussion, the alkene substrate In certain embodiments of the invention may be a chiral alkene-containing molecule or may be a prochiral alkene, by which latter term is meant that the alkene may give rise to one or two stereogenic centres upon hydroxy- or alkoxycarbonylation.

As is known to those in the art hydroxycarbonylation and alkoxycarbonylation reactions are carried out under a pressure of carbon monoxide, or carbon monoxide/hydrogen mixtures (known as syngas). Typically carbon monoxide absent hydrogen is used, and generally the pressure at which the reaction is conducted is in the range of about 1 bar (100 kPa) to about 100 bar (10,000 kPa).

The reactions may be carried out in any convenient solvent as may be suitable for the substrate and other reactants involved. Any of the commonly encountered solvents in organic chemistry can potentially be utilised, including the use of only water or—with respect to alkoxycarbonylations—only the alcohol nucleophile in large excess (i.e. as a consequence of a reactant being used as a solvent). The reactions may alternatively be conveniently carried out in a ketone solvent (e.g. a butanone or acetone).

The reaction is often (but need not necessarily be) carried out with an acidic promoter (e.g. p-toluene sulfonic acid) and optionally a metal halide. If used the metal halide or any source of halide ions may serve as an additional source of halide ions where a complex comprises halide ions (e.g. wherein X in the complexes of formula (I) comprise halide ions). A suitable metal halide is lithium chloride. Such promoters are typically used in the range 0.0001 equivalents to 2 equivalents relative to the unsaturated molecule that is to be hydroxy- or alkoxycarbonylated. However, it will be clear that changes to nature and amounts of promoters to, for example, Lewis acids (e.g. aluminium triflate ($Al(OTf)_3$) or alternative BrØnsted acids can be made without difficulty by those skilled in the art in order to optimise any particular reaction. Moreover no acidic promoter (Lewis or BrØnsted acid) need be used. For example, methods of the present invention may be usefully conducted, in the absence of an acidic promoter, in the presence of hydrogen (e.g. by using syngas) or even without hydrogen In some embodiments of the invention, the reaction effected is a hydroxycarbonylation reaction, in particular of or on an alkene substrate. The resultant carboxylic acids may be readily esterified or otherwise reacted whereby to provide carboxylic acid derivatives of general utility. However, it will be appreciated by those skilled in the art that the invention described herein has particular utility towards the alkoxycarbonylation of alkenes, since this allows access to carboxylic acid esters in a single step by selection of the appropriate alcohol, as required for the synthetic application. There is no limitation in the choice of alcohol that may be used. Primary or secondary alcohols, e.g. methanol, ethanol, n- or isopropanol may be used according to specific embodiments. Use of methanol (e.g. in place of the water used in Examples 5 to 14 below) permits methoxycarbonylation to be conducted with ease. Similarly, use of thiols or aromatic alcohols, such as optionally substituted phenols, as discussed infra, may be used to effect thiocarbonylation and aryloxycarbonylation reactions respectively.

The current invention shows that, contrary to the expectation of one skilled in the art, complexes, including those of formula (I), particularly wherein each X is Cl and $M^1=M^2=Pd$, permit improved yields in alkene carbonylation reactions relative to most diphosphine-containing monomeric catalysts, and significantly better results when compared to monomeric complexes of type $[PdCl_2(P\char`\^P)]$ (where P^P is the same diphosphine ligand acting as a chelating ligand) as that used in the analogous dimer under the same conditions.

The dimeric catalysts give significant yields even at lower reaction temperatures, and can thus be used to catalyse reactions at temperatures of between about −20° C. and about 150° C., for example, between about 40° C. and about 120° C.

The invention also shows that, contrary to expectation, such dimers with bridging P^P ligands can give significantly improved enantioselectivity relative to other diphosphine/palladium catalysts used hitherto in hydroxycarbonylation of alkenes.

The current invention in particular shows that the use of [n,n']cyclophanes combined with a suitable metal source, affords highly selective complexes for use in the hydroxy- and alkoxycarbonylation of unsaturated molecules, in particular alkenes.

It will be readily appreciated by those skilled in the art that, if desired, recognised methods of immobilisation of the ligands and complexes described herein can be used to generate heterogeneous catalysts which retain the important features of the homogeneous catalyst for example the ligands or complexes may be absorbed onto a suitable solid support or reacted with such a support to form a covalently bound ligand or catalyst.

All publications referred to herein are hereby incorporated by reference in their entirety.

The invention is further illustrated by the following non-limiting examples below.

EXAMPLE 1

Synthesis of [((R)-(−)-4,12-Bis(diphenylphosphino)-[2.2]-paracyclophane)dipalladium]tetrachloride ([Pd$_2$Cl$_4$(Ph-Phanephos)]).

(R)-(−)-4,12-Bis(diphenylphosphino)-[2.2]-paracyclophane (100 mg, 0.173 mmol) and two equivalents of [PdCl$_2$(C$_6$H$_5$CN)$_2$] (150 mg, 0.391 mmol) were added to a flask which was placed under an atmosphere of argon. They were reacted together in dry degassed dichloromethane at room temperature for 16 hours. The solvent was removed and hexane added to wash the precipitate that was filtered off and washed with a second portion of hexane to give the title compound as red crystalline powder in 88% yield (141 mg).

Key Characterisation data: Anal. Calc. (C$_{40}$H$_{34}$P$_2$Pd$_2$Cl$_4$): C, 51.70; H, 3.69%. Found: C, 52.39; H, 3.69%. $^1$H NMR, (CDCl$_3$): $\delta_H$ 7.99 (d, J=16, 2H), 7.15-7.20 (m, 11H), 7.00-7.06 (m, 13H), 3.36 (t, J=11, 2H), 2.77-2.99 (m, 6H). $^{31}$P{$^1$H}-NMR (161 MHz; CDCl$_3$): $\delta_P$ 35.6 (s). MS Cl$^-$: m/z 931.8 (M$^-$ requires 931.9).

EXAMPLE 2

Synthesis of [((S)-(+)-3,5-Bis(di(xylyl)phosphino)-[2.2]-paracyclophane)palladium]dichloride ([PdCl$_2$(Xyl-Phanephos)])

(S)-(+)-3,5-Bis(di(xylyl)phosphino)-[2.2]-paracyclophane (30 mg, 0.043 mmol) and [PdCl$_2$(C$_6$H$_5$CN)$_2$] (16.7 mg, 0.043 mmol) were added to a flask which was placed under an atmosphere of argon. They were reacted together in dry degassed dichloromethane at room temperature for 16 hours. The solvent was removed and hexane added to wash the precipitate that was filtered off and washed with a second portion of hexane to give the title compound as a yellow crystalline powder in 87% yield (33 mg).

Key Characterisation data: Anal. Calc. (C$_{48}$H$_{50}$P$_2$PdCl$_2$): C, 66.57; H, 5.82%. Found: C, 65.78; H, 5.43%(1/5 DCM). $^1$H NMR, (400MHz, CDCl$_3$): $\delta_H$ 7.58-7.60 (m, 1H), 7.52-7.55 (m, 5H), 7.39-7.43 (t, J=7, 2H), 7.21-7.27 (wide signal, 2H), 7.10 (s, 2H), 6.94 (s, 2H), 6.36 (s, 1H), 6.38 (s, 1H), 6.27 (d, J=4, 1H), 6.30 (d, J=4, 1H), 2.48-2.56 (m, 2H), 2.35-2.45 (m, 2H), 2.27 (s, 12H), 2.20 (s, 12H), 1.97-2.05 (m, 2H). $^{13}$C NMR, (75 MHz, CDCl$_3$): $\delta_c$ 143.4 (s), 138.5 (t, J=8), 137.1 (s), 137.0 (s), 136.9 (d, J=8), 136.78 (s), 136.0 (t, J=7), 135.8 (t, J=5), 133.8 (t, J=7), 133.3 (s), 132.7 (s), 131.8 (s), 131.4 (s), 131.2 (s), 128.1 (s), 34.8 (s), 31.2 (s), 20.3 (s). $^{31}$P{$^1$H}-NMR (161 MHz; CDCl$_3$): $\delta_P$ 43.6 (s). MS EI+: m/z 865.8 (M$^+$ requires 866.2), 828.8 (M-Cl$^+$ requires 829.2). [α]$_D$=−0.513 (c 0.405, CHCl$_3$)

EXAMPLE 3

Synthesis of [((S)-(+)-3,5-Bis(di(xylyl)phosphino)-[2.2]-paracyclophane)dipalladium]tetrachloride ([Pd$_2$Cl$_4$(Xyl-Phanephos)])

(S)-(+)-3,5-Bis(di(xylyl)phosphino)[2.2]-paracyclophane (50 mg, 0.073 mmol) and two equivalents of [PdCl$_2$(C$_6$H$_5$CN)$_2$] (55.7 mg, 0.145 mmol) were added to a flask which was placed under an atmosphere of argon. They were reacted together in dry degassed dichloromethane at room temperature for 16 hours. The solvent was removed and hexane added to wash the precipitate that was filtered off and washed with a second portion of hexane to give the title compound as red crystalline powder in 78% yield (59 mg). Crystals suitable for X-ray crystallography were obtained by slow diffusion of hexane into a solution of the product in dichloromethane. The resultant X-ray structure is shown in FIG. 1.

Key Characterisation data: $^1$H NMR, (300 MHz, CDCl$_3$): $\delta_H$ 7.97 (d, J=17, 2H), 6.98-6.99 (m, 6H), 6.84-6.86 (m, 3H), 6.70 (s, 2H), 6.56 (d, J=12, 3H), 3.38-3.44 (m, 2H), 3.05-3,10 (m, 2H), 2.76-2.89 (m, 4H), 2.17 (s, 12H), 2.01 (s, 12H). $^{13}$C NMR, (100 MHz, CDCl$_3$): $\delta_c$ 138.53 (s), 137.4 (d, J=48), 136.8 (s), 134.4 (s), 132.8 (s), 132.4 (s), 132.2 (s), 129.7 (d, J=52), 129.1 (s), 36.4 (s), 34.6 (s), 21.3 (s), 21.4 (s). $^{31}$P{$^1$H}-NMR (161 MHz; CDCl$_3$): $\delta_P$ 37.0 (s). MS Cl$^-$: m/z 1043.9 (M$^-$ requires 1044.0).

EXAMPLE 4

Synthesis of [((S)-(+)-Bis-di(3,5-bis-trifluoromethylphenyl)phosphino)-(2.2]-paracyclophane)dipalladium]tetrachloride ([Pd$_2$Cl$_4$(F24-Xyl-Phanephos)])

(S)-(+)-Bis(di(3,5-bis-trifluoromethylphenyl)phosphino)-[2.2]-paracyclophane (100 mg, 0.089 mmol), and two equivalents of [PdCl$_2$(C$_6$H$_5$CN)$_2$] (68.5 mg, 0.179 mmol) were added to a flask which was placed under an atmosphere of argon. They were reacted together in dry degassed dichloromethane at room temperature for 16 hours. The solvent was removed and hexane added to wash the precipitate that was filtered off and washed with a second portion of hexane to give the title compound as red crystalline powder in quantitative yield.

Key Characterisation data: $^{31}$P{$^1$H}-NMR (161 MHz; CDCl$_3$): $\delta_P$ 35.6 (s). {Note: starting ligand: $^{31}$P{$^1$H}-NMR (161 MHz; CDCl$_3$): $\delta_P$ 0.65 (s)}MS Cl$^-$: m/z 1475.9 (M$^-$ requires 1475.8).

EXAMPLE 5

Hydroxycarbonylation of Styrene using [Pd$_2$(Xyl-Phanephos)Cl$_4$]

LiCl (8.4 mg, 0.20 mmol, 20%), p-TsOH (34.4 mg, 0.20 mmol, 20%) and [Pd$_2$(Xyl-Phanephos)Cl$_4$] (10.4 mg, 0.01 mmol, 1%) were weighed into a 5 ml sealable vial. A stirring bar was placed inside and vial sealed with a crimp cap and put under inert atmosphere using a needle connected to vacuum line. Styrene (114 µl, 1 mmol, 100%), water (45 µl, 2.5 mmol, 250%) and 2-butanone (1.5 ml) were added. The caps were pierced with two needles and placed in the autoclave which was quickly sealed. The autoclave was purged three times with CO and then pressurized to 30 bar and heated in a preheated oil bath to 50° C. for 72 hours. After this time, the autoclave was cooled to room temperature and the pressure released slowly. NMR analysis shows a high conversion to the carboxylic acid product. To remove the catalyst; The solvent was carefully removed from the reaction mixture and the residue dissolved in toluene and filtered to remove precipitate. The toluene filtrate was extracted 3 times (~20 ml) with saturated NaHCO$_3$ solution and the combined aqueous extracts were acidified with conc. HCl. The aqueous solution was then extracted 3 times with DCM (~20 ml) and the combined organic layers were dried over MgSO$_4$, filtered and the solvent removed to give the product mixture of 2-phenylpropanoic ('branched') and 3-phenylpropanoic acid ('linear') (105.4 mg, 0.70 mmol, 71%; Branched/Linear=1.1 (determined by $^1$H-NMR); The ratio of optical isomers was 90/10 (i.e. 80% e.e. determined by HPLC analysis (CHIRACEL OD-H; hexane/i-PrOH/TFA 97:3:0.1)). NMR data for products:

2-phenylpropanoic acid: $^1$H NMR δ: 1.45 (3H, d, CH$_3$), 3.7 (1 H, q, CH), 7.2 (5H, m, ArH).

3-phenylpropanoic acid: $^1$H NMR δ: 2.6 (2H, t, CO-CH$_2$), 2.9 (2H, t, CH$_2$), 7.2 (5H, m, ArH).

MS ES: m/z 149.0 (M⁻ requires 150.2)

EXAMPLE 6

Hydroxycarbonylation of Styrene Using [Pd(Xyl-Phanephos)Cl$_2$]

LiCl (8.4 mg, 0.20 mmol, 20%), p-TsOH (34.4 mg, 0.20 mmol, 20%) and [Pd(Xyl-Phanephos)Cl$_2$] (8.7 mg, 0.01 mmol, 1%) were weighed into a 5 ml vial. A stirring bar was placed inside and vial sealed with a crimp cap and put under inert atmosphere using a needle connected to vacuum line. Styrene (114 μl, 1 mmol, 100%), water (45 μl, 2.5 mmol, 250%) and 2-butanone (1.5 ml) were added by syringe. The caps were pierced with two needles and placed in the autoclave which was quickly sealed. The autoclave was purged three times with CO and then pressurized to 30 bar and heated in a preheated oil bath to 50° C. for 72 hours. After this time, the autoclave was cooled to room temperature and the pressure released slowly. NMR analysis shows a low conversion to the carboxylic acid product. To remove the catalyst; The solvent was carefully removed from the reaction mixture and the residue dissolved in toluene and filtered to remove precipitate. The toluene filtrate was extracted 3 times (~20 ml) with saturated NaHCO$_3$ solution and the combined aqueous extracts were acidified with conc. HCl. The aqueous solution was then extracted 3 times with DCM (~20 ml) and the combined organic layers were dried over MgSO$_4$, filtered and the solvent removed to give the product mixture of 2-phenylpropanoic ('branched') and 3-phenylpropanoic acid ('linear') (11.9 mg, 0.08 mmol, 8%; Branched/Linear=0.4 (determined by $^1$H-NMR); The ratio of optical isomers was 75/25 (i.e. 50% e.e. determined by HPLC analysis (CHIRACEL OD-H; hexane/i-PrOH/TFA 97:3:0.1)).

EXAMPLE 7

Hydroxycarbonylation of Styrene Using [Pd$_2$(Xyl-Phanephos)Cl$_4$]

LiCl (8.4 mg, 0.20 mmol, 20%), p-TsOH (34.4 mg, 0.20 mmol, 20%) and [Pd$_2$-(Xyl-Phanephos)Cl$_4$] (10.4 mg, 0.01 mmol, 1%) were weighed into a 5 ml microwave vial. A stirring bar was placed inside and vial sealed with a crimp cap and put under inert atmosphere using a needle connected to vacuum line. Styrene (114 μl, 1 mmol, 100%), water (45 μl, 2.5 mmol, 250%) and 2-butanone (1.5 ml) were added. The caps were pierced with two needles and placed in the autoclave which was quickly sealed. The autoclave was purged the autoclave three times with CO and then pressurized to 30 bar and heated in a preheated oil bath to 60° C. for 16 hours. After this time, the autoclave was cooled to room temperature and the pressure released slowly. The solvent was carefully removed from the reaction mixture and the residue dissolved in toluene and filtered to remove precipitate. The toluene filtrate was extracted 3 times (~20 ml) with saturated NaHCO$_3$ solution and the combined extracts were acidified with conc. HCl. The solution was then extracted 3 times with DCM (~20 ml) and the combined organic layers were dried over MgSO$_4$, filtered and the solvent removed to give the product mixture of 2-phenylpropanoic and 3-phenylpropanoic acid (86.1 mg, 0.57 mmol, 58%; Branched/Linear=1/1 (determined by $^1$H-NMR); The ratio of optical isomers was 88/12 (i.e. 76% e.e. as determined by HPLC analysis (CHIRACEL OD-H; hexane/i-PrOH/ TFA 97:3:0.1)).

EXAMPLE 8

Hydroxycarbonylation of Styrene Using [Pd$_2$(Phanephos)Cl$_4$]

LiCl (8.4 mg, 0.20 mmol, 20%), p-TsOH (34.4 mg, 0.20 mmol, 20%) and [Pd$_2$-(Phanephos)Cl$_4$] (9.3 mg, 0.01 mmol, 1%) were weighed into a 5 ml microwave vial. A stirring bar was placed inside and vial sealed with a crimp cap and put under inert atmosphere using a needle connected to vacuum line. Styrene (114 μl, 1 mmol, 100%), water (45 μl, 2.5 mmol, 250%) and 2-butanone (1.5 ml) were added. The caps were pierced with two needles and placed in the autoclave which was quickly sealed. The autoclave was purged the autoclave three times with CO and then pressurized to 30 bar and heated in a preheated oil bath to 70° C. for 17 hours. After this time, the autoclave was cooled to room temperature and the pressure released slowly. The solvent was carefully removed from the reaction mixture and the residue dissolved in toluene and filtered to remove precipitate. The toluene filtrate was extracted 3 times (~20 ml) with saturated NaHCO$_3$ solution and the combined extracts were acidified with conc. HCl. The solution was then extracted 3 times with DCM (~20 ml) and the combined organic layers were dried over MgSO$_4$, filtered and the solvent removed to give the product mixture of 2-phenylpropanoic and 3-phenylpropanoic acid (108.4 mg, 0.72 mmol, 73%; Branched/Linear=1.1 (determined by $^1$H-NMR); The ratio of optical isomers was 76/24 (i.e. 52% e.e. as determined by HPLC analysis (CHIRACEL OD-H; hexane/i-PrOH/TFA 97:3:0.1)).

EXAMPLE 9

Hydroxycarbonylation of Styrene Using ([Pd$_2$Cl$_4$(F24-Xyl-Phanephos)])

LiCl (0.20 mmol, 20%), p-TsOH (0.10 mmol, 10%) and [Pd$_2$Cl$_4$(F24-Xyl-Phanephos)] (0.01 mmol, 1%) were weighed into a 5 ml microwave vial. A stirring bar was placed inside and vial sealed with a crimp cap and put under inert atmosphere using a needle connected to vacuum line. Styrene (114 μl, 1 mmol, 100%), water (45 μl, 2.5 mmol, 250%) and 2-butanone (1.5 ml) were added. The caps were pierced with two needles and placed in the autoclave which was quickly sealed. The autoclave was purged the autoclave three times with CO and then pressurized to 30 bar and heated in a preheated oil bath to 70° C. for 16 hours. After this time, the autoclave was cooled to room temperature and the pressure released slowly. The solvent was carefully removed from the reaction mixture and the residue dissolved in toluene and filtered to remove precipitate. The toluene filtrate was extracted 3 times (~20 ml) with saturated NaHCO$_3$ solution and the combined extracts were acidified with conc. HCl. The solution was then extracted 3 times with ethyl acetate (~20 ml) and the combined organic layers were dried over MgSO$_4$, filtered and the solvent removed to give the product mixture of 2-phenylpropanoic and 3-phenylpropanoic acid (99% conversion to product;. Branched/Linear=121/1) The ratio of optical isomers was 86.5/13.5.

EXAMPLE 10

Hydroxycarbonylation of Styrene Using [Pd$_2$(Phanephos)Cl$_4$]

LiCl (8.4 mg, 0.20 mmol, 20%), p-TsOH (34.4 mg, 0.20 mmol, 20%) and [Pd$_2$-(Phanephos)Cl$_4$] (9.3 mg, 0.01 mmol, 1%) were weighed into a 5 ml microwave vial. A stirring bar was placed inside and vial sealed with a crimp cap and put under inert atmosphere using a needle connected to vacuum line. Styrene (114 µl, 1 mmol, 100%), water (45 µl, 2.5 mmol, 250%) and 2-methyltetrahydrofuran (1.5 ml) were added. The caps were pierced with two needles and placed in the autoclave which was quickly sealed. The autoclave was purged the autoclave three times with CO and then pressurized to 30 bar and heated in a preheated oil bath to 70° C. for 17 hours. After this time, the autoclave was cooled to room temperature and the pressure released slowly. The solvent was carefully removed from the reaction mixture and the residue dissolved in toluene and filtered to remove precipitate. The toluene filtrate was extracted 3 times (~20 ml) with saturated NaHCO$_3$ solution and the combined extracts were acidified with conc. HCl. The solution was then extracted 3 times with ethyl acetate (~20 ml) and the combined organic layers were dried over MgSO$_4$, filtered and the solvent removed to give the carboxylic acid product (80% conversion to product) as a 3:1 mixture of branched and linear isomers. The ratio of optical isomers was 73/27.

EXAMPLE 11

Hydroxycarbonylation of Styrene Using [Pd$_2$(Xyl-Phanephos)Cl$_4$] With No Acid Catalyst and Syngas as Source of CO LiCl (4.2 mg, 0.1 mmol) and [(Xyl-(S)-Phanephos)Pd$_2$Cl$_4$] (5.2 mg, 0.005 mmol) were weighed into a 5 ml microwave vial. A magnetic stirrer bar was added, the vial was sealed with a crimp cap and put under an inert atmosphere. Styrene (57 µl, 0.5 mmol), water (22.5 µl, 1.25 mmol) and butanone (1.5 ml) were then added by syringe, as was the internal standard Et$_4$Si (23.5 µl, 0.125 mmol). The caps were pierced with two needles and the vials placed into an autoclave, under an inert atmosphere, and the autoclave quickly sealed. The autoclave was purged three times with CO/H$_2$, then pressurised to 30 bar and heated in a preheated oil bath at 70° C. After 18 hours the autoclave was cooled to room temperature and the pressure released slowly. A sample of the crude product was removed for analysis by $^1$H NMR spectroscopy. The solvent was removed from the remaining reaction mixture under vacuum and the residue dissolved in toluene. The product was extracted 3 times with saturated NaHCO$_3$ solution and the combined aqueous phases were acidified with conc. HCl. The solution was then extracted 3 times with EtOAc. The combined organic layers were dried over MgSO$_4$, filtered and the solvent removed under vacuum, to give the carboxylic acid product as a 52:48 mixture of branched and linear isomers in (52% conversion to product, 32% yield). The ratio of optical isomers was 84.5:15.5.

EXAMPLE 12

Hydroxycarbonylation of Alpha-Methyl-Styrene Using [Pd$_2$(Xyl-Phanephos)Cl$_4$]

LiCl (4.2 mg, 0.1 mmol), p-TsOH (17.2 mg, 0.1 mmol) and [(Xyl-(S)-Phanephos)Pd$_2$Cl$_4$] (0.005 mmol) were weighed into a 5 ml microwave vial. A magnetic stirrer bar was added, the vial was sealed with a crimp cap and put under an inert atmosphere. α-methylstyrene (65 µl, 0.5 mmol), water (22.5 µl, 1.25 mmol) and butanone (1.5 ml) were then added by syringe, as was the internal standard Et$_4$Si (23.5 µl, 0.125 mmol). The caps were pierced with two needles and the vials placed into an autoclave, under an inert atmosphere, and the autoclave quickly sealed. The autoclave was purged three times with CO, then pressurised to 30 bar and heated in a preheated oil bath to 90° C. After 20 hours the autoclave was cooled to room temperature and the pressure released slowly. A sample of the crude product was removed for analysis by $^1$H NMR spectroscopy. The solvent was removed from the remaining reaction mixture under vacuum and the residue dissolved in toluene. The product was extracted 3 times with saturated NaHCO$_3$ solution and the combined aqueous phases were acidified with conc. HCl. The solution was then extracted 3 times with EtOAc. The combined organic layers were dried over MgSO$_4$, filtered and the solvent removed under vacuum, to give the carboxylic acid product as a 4:94 mixture of quaternary and linear isomers (84% conversion, 77% isolated yield).

EXAMPLE 13

Hydroxycarbonylation of Norbornene Using [Pd$_2$(Ph-Phanephos)Cl$_4$]

Lithium chloride (8.4 mg, 0.20 mmol), para-toluene-sulfonic acid (34.4 mg, 0.20 mmol), [(Ph—(R)-Phanephos)Pd$_2$Cl$_4$] (0.01 mmol) and norbornene (94.2 mg, 1 mmol) were weighed into a Biotage 5 ml microwave vial. A stirring bar was added and the vial was sealed with a crimp cap and put under inert atmosphere. Degassed water (between 2.5 equiv. and 15 equiv.), degassed 2-butanone (1.5 ml) and internal standard (approximately 10 µl of 1-methylnaphtalene) were added using a syringe. The solution was mixed before 20 µl of the solution was diluted in CDCl$_3$ and analysed using NMR (to give a t$_0$ spectra that calibrates the internal standard against starting material). The caps were pierced with two needles and quickly placed in an autoclave that had previously been placed under an argon atmosphere before being opened under a flow of argon. The autoclave was sealed, purged three times with CO and then pressurised to 30 bar and heated in a preheated oil bath or heating jacket at 65° C. with constant magnetic stirring. After the desired time, the autoclave was cooled to room temperature and the pressure released slowly. The mixture was then analysed by taking a sample, diluting with CDCl$_3$ and obtaining an $^1$H NMR spectrum. This shows the formation of the desired acid as a 99:1 mixture of exo and endo isomers (52% conversion to acid, 48% oligomeric dimer-acid) The solvent was carefully removed from the reaction mixture and the residue was purified by column chromatography (SiO$_2$, using hexane: ethylacetate 8:1 as eluent) to give colourless crystals of bicyclo[2.2.1]heptane-2-carboxylic acid (39% isolated yield). The ratio of optical isomers was determined by forming the mandelate ester of the carboxylic acid and calculating the diastereomeric excess by $^1$H-NMR integration, and in this case was 89:11.

NMR data for catalysis product:(1R, 2R 4S)bicyclo[2.2.1]heptane-2-carboxylic acid $^1$H NMR (300 MHz, CDCl$_3$) δ 1.31-1.12 (m, 3H), 1.65-1.40 (m, 4H), 1.9-1.78 (m, 1H), 2.42-2.50 (m, 2H), 2.55 (br s, 1H), 11-12.2 (br, OH). $^{13}$C NMR (75 MHz, CDCl$_3$) δ29.0, 29.9 34.5, 36.9, 41.3, 46.8, 182.8.

MS ES−: m/z 139.01 ([M-H]$^+$ requires 139.07)

EXAMPLE 14

The hydroxycarbonylations can be carried with a wide range of promoters. Examples are shown in the Table below using reduced reaction times.

| Co-catalyst 1 | Co-catalyst 2 | (%) Product after 5 hours | B:L | ee |
|---|---|---|---|---|
| — | — | 13 | 55:45 | 58 |
| LiCl | — | 8 | 56:44 | 72 |
| LiCl | p-TsOH | 21 | 51:49 | 74 |
| $CF_3CO_2$— | $CF_3CO_2H$ | 18 | 44:56 | 53 |
| LiCl | $H_2SO_4$ | 16 | 51:49 | 64 |
| LiCl | $H_3PO_4$ | 12 | 49:51 | 62 |
| LiCl | $Al(OTf)_3$ | 17 | 52:48 | 50 |
| $NH_4Cl$ | — | 12 | 58:62 | 56 |
| CsCl | p-TsOH | 32 | 53:47 | 60 |

Analysis of acidic promoters for the hydroxycarbonylation of styrene (0.5 mmol), $H_2O$ (1.25 mmol), CO (30 bar), [$Pd_2$(Xyl-Phanephos)$Cl_4$] (0.005 mmol), $Et_4Si$ (0.125 mmol), butanone (1.5 ml), 70° C. (%) Product determined by comparison with internal standard by $^1H$ NMR analysis of crude reaction mixture; B:L determined by $^1H$ NMR; ee determined by HPLC.

EXAMPLE 15

Methoxycarbonylation of Styrene Using [$Pd_2$(Xyl-Phanephos)$Cl_4$] as Catalyst at Room Temperature Lithium chloride (8.4 mg, 0.20 mmol), para-toluenesulfonic acid (34.4 mg, 0.20 mmol) and [(Xyl-(S)-Phanephos)$Pd_2Cl_4$] (0.01 mmol) were weighed into a 5 ml microwave vial. A stirring bar was added and the vial was sealed with a crimp cap and put under inert atmosphere. Styrene (1 mmol), dry and degassed methanol (1.5 ml) and an internal standard (approximately 10 μl of either tetraethylsilane and 1-methylnaphtalene) were added using a syringe. The solution was mixed before 20 μl of the solution was diluted in $CDCl_3$ and analysed using NMR (to give a $t_0$ spectra that calibrates the internal standard against starting material). The caps were pierced with two needles and quickly placed in an autoclave that had previously been placed under an argon atmosphere before being opened under a flow of argon. The autoclave was sealed, purged three times with CO and then pressurised to 30 bar and heated in a preheated oil bath at 25° C. with constant magnetic stirring. After the desired time, the autoclave was cooled to room temperature and the pressure released slowly. The mixture was then analysed by taking a sample, diluting with $CDCl_3$ and obtaining a $^1H$ NMR spectrum. The solvent was carefully removed from the reaction mixture and the crude product was filtered through a small column packed with $SiO_2$ eluting with hexane: ethylacetate 8:1. The solvent was removed to give carboxylic acid ester product as a 47:53 mixture of branched and linear isomers (71% conversion to ester, 62% isolated yield). The ratio of optical isomers was 94.5:5.5.

The enantiomeric excess was determined by HPLC, using a Chirapak AD-H, 250×4.6 mm, 5 μm with guard cartridge, n-hexane 100%, 0.5 mL min$^{-1}$, 210 nm, $t_R$[(+)-S]=17.9 min, $t_R$[(−)-R]=20.0 min, $t_R$[linear]=25.1 min. GCMS shows the expected linear and branched esters. EIMS 164 (M+).

NMR data for catalysis products: Methyl-2-phenylpropanoate: $^1H$ NMR (300 MHz, $CDCl_3$) δ 1.42 (d, J=9, $CH_3$, 3H), 3.57 (s, $CH_3$, 3H), 3.65 (q, J=9 Hz, CH, 1H), 7.07-7.28 (m, ArH, 5H). $^{13}C$ NMR (75 MHz, $CDCl_3$) δ 18.6, 45.5, 52.1, 127.2, 127.5, 128.7, 140.5, 175.1.

Methyl-3-phenylpropanoate:
$^1H$ NMR (300 MHz, $CDCl_3$) δ 2.55 (t, J=7.5, $CH_2$, 2H), 2.87 (t, J=7.5, $CH_2$, 2H), 3.58 (s, $OCH_3$, 3H), 7.07-7.28 (m, ArH, 5H). $^{13}C$ NMR (75 MHz, $CDCl_3$) δ 31.0, 35.7, 51.7, 126.3, 128.3, 128.5, 173.4.

EXAMPLE 16

Iso-propoxycarbonylation of styrene using [$Pd_2$(Xyl-Phanephos)$Cl_4$]

LiCl (8.4 mg, 0.20 mmol, 20%), p-TsOH (34.4 mg, 0.20 mmol, 20%) and [$Pd_2$(Xyl-Phanephos)$Cl_4$] (10.3 mg, 0.01 mmol, 1%) were weighed into a 5 ml sealable vial. A stirring bar was placed inside and vial sealed with a crimp cap and put under inert atmosphere using a needle connected to vacuum line. Styrene (114 μl, 1 mmol, 100%) and anhydrous i-PrOH (1.5 ml) were added. The caps were pierced with two needles and placed in the autoclave which was quickly sealed. The autoclave was purged three times with CO and then pressurized to 30 bar and heated in a preheated oil bath to 75° C. for 24 hours. After this time, the autoclave was cooled to room temperature and the pressure released slowly. The mixture was then analysed by taking a sample, diluting with $CDCl_3$ and obtaining a $^1H$ NMR spectrum (99% conversion). The solvent of the reaction mixture was remove and the solids dissolved in toluene (1 ml) and suspension was filtered through a plug of silica and the solvent removed to give the carboxylic acid ester product (97%) as a 0.52/1 mixture of iso-propyl 2-phenylpropanoate ('branched') and iso-propyl 3-phenylpropanoate ('linear'). The ratio of optical isomers was 79:21. This was determined by HPLC analysis (CHIRALPAK AD and CHIRALPAK AD-H connected in series; 100% hexane, 0.5ml/min). GCMS shows the expected linear and branched esters: MS EI$^+$: m/z 192.0 (M$^+$ requires 192.2). NMR data for products: Iso-propyl 2-phenylpropanoate: $^1H$ NMR : 1.13 (d, 3H, J=3 Hz), 1.22 (d, 3H, J=6 Hz), 1.48 (d, 3H, J=3 Hz), 3.67 (q, 1H, J=6 Hz), 5.05-4.93 (m, 1H), 7.35-7.21 (m, 5H).

Iso-propyl 3-phenylpropanoate: $^1H$ NMR: 1.17 (d, 3H, J=3 Hz), 2.55 (t, 2H, J=6), 2.91 (t, 2H, J=6), 5.05-4.93 (m, 1H), 7.35-7.19 (m, 5H).

EXAMPLE 17

Phenoxycarbonylation of styrene using [$Pd_2$(Xyl-Phanephos)$Cl_4$]

LiCl (8.4 mg, 0.20 mmol, 20%), p-TsOH (34.4 mg, 0.20 mmol, 20%) and [$Pd_2$(Xyl-Phanephos)$Cl_4$] (10.3 mg, 0.01 mmol, 1%) were weighed into a 5 ml sealable vial. A stirring bar was placed inside and vial sealed with a crimp cap and put under inert atmosphere using a needle connected to vacuum line. Styrene (114 μl, 1 mmol, 100%), PhOH (94.1 mg, 1 mmol, 100%) and 2-butanone (1.5 ml) were added. The caps were pierced with two needles and placed in the autoclave which was quickly sealed. The autoclave was purged three times with CO and then pressurized to 30 bar and heated in a preheated oil bath to 75° C. for 24 hours. After this time, the autoclave was cooled to room temperature and the pressure released slowly. The mixture was then analysed by filtration through silica, removal of solvent, diluting with $CDCl_3$ and obtaining a $^1H$ NMR spectrum (84% conversion to the carboxylic ester product as a 0.76:1 ratio of phenyl 2-phenylpropanoate ('branched') and phenyl 3-phenylpropanoate ('linear'). GCMS shows the expected linear and branched esters: MS EI$^+$: m/z 226.0 (M$^+$ requires 226.2).

NMR data for products: phenyl 2-phenylpropanoate: $^1$H NMR : 1.59 (d, 3H, J=9 Hz), 3.94 (q, 1H, J=9 Hz), 7.18-7.40 (m, 10H).

phenyl 3-phenylpropanoate: $^1$H NMR: 2.86 (t, 2H, J=7.5Hz), 3.05 (t, 2H, J=7.5), 6.94-7.00 (m, 2H), 7.18-7.40 (m, 8H).

The invention claimed is:

1. A method for the hydroxycarbonylation, alkoxycarbonylation, aryloxycarbonylation or thiocarbonylation of an alkene comprising effecting a hydroxycarbonylation, alkoxycarbonylation, aryloxycarbonylation or thiocarbonylation reaction on the alkene in which a complex comprising a ligand comprising a [n,n'] cyclophane comprising two non-fused monocyclic aromatic rings bridged by two linear and aliphatic linkages, in which each of the non-fused monocyclic aromatic rings is substituted with a phosphorus atom-containing substituent, is used to catalyse the hydroxycarbonylation, alkoxycarbonylation, aryloxycarbonylation or thiocarbonylation reaction.

2. The method of claim 1, which is a method for the hydroxycarbonylation or alkoxycarbonylation of an alkene comprising effecting a hydroxycarbonylation reaction or alkoxycarbonylation reaction on the alkene in which a complex comprising a ligand comprising a [n,n'] cyclophane comprising two non-fused monocyclic aromatic rings bridged by two linear and aliphatic linkages, in which each of the non-fused monocyclic aromatic rings is substituted with a phosphorus atom-containing substituent, is used to catalyse the hydroxycarbonylation reaction or the alkoxycarbonylation reaction.

3. The method of claim 1 wherein the ligand is a [n,n'] para(phenylene) cyclophane.

4. The method of claim 1 wherein n and n' are each 2, 3 or 4 or n and n' are each 2.

5. The method of claim 1 wherein n and n' are each ethylene, n-propylene or n-butylene.

6. The method of claim 1 wherein the ligand is a pseudo-ortho disubsutituted [n,n'] para(phenylene) cyclophane.

7. The method of claim 1 wherein the complex comprises one or two transition metal atoms in oxidation state (II) or (0) and comprises one or two transition metal atoms selected from Pd, Pt, Ni, Rh, Ir, Co, Cu, Zn, Fe, Os, Re, Tc, Mn and Ru.

8. The method of claim 7 wherein the complex comprises a or transition metal atom selected from Pd, Pt and Ni.

9. The method of claim 8 wherein the complex comprises one or two Pd atoms in oxidation state (II).

10. A method for the hydroxycarbonylation, alkoxycarbonylation, aryloxycarbonylation or thiocarbonylation of an alkene comprising effecting a hydroxycarbonylation, alkoxycarbonylation, aryloxycarbonylation or thiocarbonylation reaction on the alkene in which a complex comprising two metal centres and a ligand comprising two phosphorus atoms is used to catalyse the hydroxycarbonylation, alkoxycarbonylation, aryloxycarbonylation or thiocarbonylation reaction.

11. The method of claim 10, which is a method for the hydroxycarbonylation or alkoxycarbonylation of an alkene comprising effecting a hydroxycarbonylation reaction or alkoxycarbonylation reaction on the alkene in which a complex comprising two metal centres and a ligand comprising two phosphorus atoms is used to catalyse the hydroxycarbonylation reaction or the alkoxycarbonylation reaction.

12. The method of claim 10 wherein the complex is formula (I)

(wherein:

$M^1$ is a Group 10 transition metal;

$M^2$ is a transition metal;

each X is independently an anionic ligand that can adopt both bridging or terminal coordination modes; and P^P is a ligand containing two phosphorus atoms that binds to both $M^1$ and $M^2$).

13. The method of claim 12 wherein each X is chloride, bromide or iodide.

14. The method of claim 12 wherein the phosphorus atoms are each part of a phosphino, phosphonite, phosphorus amide or phosphonamidite substituent.

15. The method of claim 14 wherein the phosphorus atoms are each part of a phosphino substituent.

16. The method of claim 15 wherein the phosphorus atoms are each part of a optionally substituted diarylphosphino substituent.

17. The method of claim 16 wherein the phosphorus atoms are each part of a optionally substituted diphenylphosphino substituent.

18. The method of claim 17 wherein the phosphorus atoms are each part of a alkyl-substituted diphenylphosphino substituent or each part of a diphenylphosphino substituent.

19. The method of claim 1 wherein the method is for the hydroxycarbonylation of an alkene.

20. A complex comprising two metal centres and a ligand comprising a [n,n'] cyclophane comprising two non-fused monocyclic aromatic rings bridged by two linear and aliphatic linkages, in which each of the non-fused monocyclic aromatic rings is substituted with a phosphorus atom-containing substituent.

21. The method of claim 12 wherein the method is for the hydroxycarbonylation of an alkene.

* * * * *